(12) United States Patent
Nurmi et al.

(10) Patent No.: US 6,881,876 B2
(45) Date of Patent: Apr. 19, 2005

(54) MATERIAL STRUCTURE FOR USE IN ABSORBENT ARTICLES, AND AN ABSORBENT ARTICLE COMPRISING SUCH A MATERIAL STRUCTURE

(75) Inventors: Hannele Nurmi, Rönnäng (SE);
Anders Silfverstrand, Mölnlycke (SE);
Anna-Karin Jönbrink, Lerum (SE);
Eva Simmons, Mölndal (SE);
Elisabeth Lakso, Stenungsund (SE);
Gunilla Himmelman, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/860,565

(22) Filed: May 21, 2001

(65) Prior Publication Data

US 2002/0032424 A1 Mar. 14, 2002

Related U.S. Application Data

(63) Continuation of application No. PCT/SE99/02148, filed on Nov. 23, 1999.

(30) Foreign Application Priority Data

Dec. 3, 1998 (SE) .............................................. 9804201

(51) Int. Cl.⁷ .............................................. A61F 13/15
(52) U.S. Cl. ..................................... 604/370; 604/378
(58) Field of Search ............................... 604/365, 366, 604/370, 372, 378, 383

(56) References Cited

U.S. PATENT DOCUMENTS 5,698,322 A * 12/1997 Tsai et al. .............. 264/172.11
5,763,524 A * 6/1998 Arkens et al. .............. 524/547
5,801,116 A * 9/1998 Cottrell et al. .............. 502/401
5,827,254 A * 10/1998 Trombetta et al. .......... 604/378
5,843,058 A * 12/1998 Quist .......................... 604/369
6,037,518 A * 3/2000 Guidotti et al. ............. 604/378
6,534,572 B1 * 3/2003 Ahmed et al. .............. 524/275

FOREIGN PATENT DOCUMENTS

| JP | 5-22109 | 1/1993 |
|----|---------|--------|
| WO | 90/01521 | 2/1990 |
| WO | 91/08726 | 6/1991 |
| WO | 95/23249 | 8/1995 |
| WO | 98/24951 | 6/1998 |

* cited by examiner

*Primary Examiner*—Larry I. Schwartz
*Assistant Examiner*—C. Lynne Anderson
(74) *Attorney, Agent, or Firm*—Burns, Doane, Swecker & Mathis, L.L.P.

(57) ABSTRACT

The invention relates to a material structure for use in absorbent articles, and an absorbent article comprising such a material structure. The material structure (1) comprises a liquid-pervious cover layer (2), a liquid-impervious cover layer (3), and an absorbent structure (4, 4') enclosed between the cover layers (2, 3). Thereby, the absorbent structure (4, 4') comprises polylactide fibres or filaments, the properties of which contributing to a rapid acquisition of liquid through the liquid-pervious cover layer (2) for absorption into the absorbent structure (4, 4') also when the material structure (1) is subjected to repeated wettings. The invention can advantageously be applied within the field of absorbent hygiene articles, such as different types of diapers and incontinence guards, sanitary napkins, pantyliners, and the like.

11 Claims, 1 Drawing Sheet

MATERIAL STRUCTURE FOR USE IN ABSORBENT ARTICLES, AND AN ABSORBENT ARTICLE COMPRISING SUCH A MATERIAL STRUCTURE

This application is a continuation of International Application No. PCT/SE99/02148, filed on Nov. 23, 1999, which International Application was published by the International Bureau in English on Jun. 8, 2000.

TECHNICAL FIELD

The present invention relates to a material structure for use in absorbent articles, and an absorbent article comprising such a material structure. The invention can advantageously be applied within the field of absorbent hygiene articles, such as different types of napkins and incontinence guards, sanitary napkins, pantyliners and the like.

BACKGROUND OF THE INVENTION

When disposable absorbent articles are concerned, previously large efforts have been made in order to obtain good properties for absorption of exudated body fluids. For this reason, on their front sides, absorbent articles of the type in question are provided with special liquid-pervious front side layers, which are designed for a rapid liquid acquisition and for providing a dry surface on the side of the article which faces towards a user also after repeated absorptions of body fluids. Normally, this effect is achieved by means of providing suitably designed openings for liquid acquisition through the front side material, and by means of selecting polymer materials in the front side material which not easily absorb exudated body fluids, but instead let the body fluids pass through to underlying layers in the absorbent structure.

On their backside, absorbent articles of the type in question usually are provided with a liquid-impervious backside material, which prevents exudated body fluids from striking through and soiling the clothing of the user.

Conventional front side and backside materials of absorbent articles usually comprise nonwoven or film materials of synthetic polymers, which normally are based on crude oil and are not biologically degradable in the short term.

Since landfill and sometimes composting is utilised in order to dispose of disposable absorbent articles after use, previously attempts have been made to find replacement materials, which are biologically degradable in the short term, for the synthetic polymers which normally are included in the front side and backside materials of absorbent structures and articles.

Accordingly, the international patent application nr. PCT/US90/07169 discloses disposable absorbent structures and absorbent articles in which the front side and/or backside material comprise(s) a polyester which is based on lactic acid or glycolic acid. The utilised polyesters are said to be designed for being degradable by means of a simple hydrolysis, for example in landfill.

Furthermore, the Japanese patent application JP 93-022109 discloses a biologically degradable, thermoplastic polymer with a higher melting point than 100° C. It is stated that the polymer preferably comprises poly-3-hydroxy-propionate (or -butylate, -capreolate, -heptanoate or -octanoate) and copolymers thereof, poly-gamma-butyrolactone, polyethylene succinate, polybutylene succinate, polyneopentyl succinate (or -oxalate), polyglycolide, polylactide and copolymers or mixtures thereof. Staple fibres of the biologically degradable polymer are claimed to be useful in surface materials for disposable diapers or sanitary napkins, or in other materials for hygiene use. The biologically degradable staple fibre disclosed in JP 93-022109 is claimed to be resistant to higher temperatures than 80° C., hydrophobic, heat-fusible, and completely biologically degradable after use by means of environmental influence.

As has become evident from the foregoing, an absorbent article, for example a diaper or a pair of training pants for infants or incontinent adults, an incontinence guard, a sanitary napkin, a pantyliner, or the like, usually comprises a liquid-pervious cover layer on the side of the article which is intended to face towards a user when the article is used. On the side of the article which is intended to face away from the user when the article is used, the absorbent article is provided with a liquid-impervious cover layer, wherein the liquid-pervious cover layer and the liquid-impervious cover layer together enclose an absorbent structure. The absorbent structure comprises an absorbent core, which usually consists of cellulose fluff pulp with an addition of highly absorbent polymer, so-called superabsorbent.

Between the absorbent core and the liquid-pervious cover layer, a liquid-acquiring layer, which can consist of a porous, open wadding structure with high wettability, is usually provided. In order to obtain a rapid liquid acquisition and a high surface dryness of the liquid-pervious cover layer on the outside, it is important that the liquid-acquiring layer exhibits a high hydrophilicity and, consequently, a low contact angle to the liquid which is to be absorbed. A high hydrophilicity can be obtained by means of manufacturing the liquid-acquiring layer from hydrophilic fibres, for example viscose fibres or lyocell fibres. Since structures with such regenerated cellulosic fibres have a tendency to collapse when wetted, fibres based on synthetic polymers are often utilised or mixed into the liquid-acquiring layer, in spite ot the fact that such synthetic fibres exhibit a high intrinsic hydrophobicity which actually is undesired for a liquid-acquiring layer.

In order to improve the wettability, i.e. increase the hydrophilicity, of liquid-acquiring layers which comprise conventional synthetic fibres, the synthetic fibres or the entire liquid-acquiring layer is usually treated with a suitable surfactant. A disadvantage which can occur as a consequence of such surfactant treatment is that certain surfactants, particularly at high addition levels, may give sensitive users skin irritations. Another previously known problem with such surfactant treatment is that the wettability is impaired after repeated wettings with body fluid, i.e that the hydrophilicity obtained by means of the surfactant treatment is non-permanent.

In order to obtain maximum liquid transport between the different material layers in the material structure of an absorbent article, the material layers should be brought into closest possible contact with each other. Thereby, the use of an adhesive for binding the material layers can result in an impaired wettability, since the type of adhesive s in question usually are of a hydrophobic nature. For this reason, thermobonding of thermoplastic fibres included in the material layers is preferred instead of adhesive bonding. Something which can be perceived as a disadvantage with thermobonding of conventional synthetic fibres is that the included polymers require a relatively high temperature, usually considerably higher than 100° C., in order to be possible to bind thermally. When manufacturing material structures for absorbent articles, such high temperatures can be difficult to achieve without impairing for example the wettability of the cellulosic fibres included in an absorbent core.

As has become evident from the foregoing, another disadvantage with conventional synthetic fibres is that they are not biologically degradable in the short term and, furthermore, are based on raw materials which are non-renewable in the short term.

SUMMARY OF THE INVENTION

Accordingly, the first object of the present invention is to provide a material structure for use in absorbent articles, which material structure comprises an absorbent structure having a high, permanent liquid acquisition ability already at no or only a low surfactant addition.

In accordance with claim 1, this first object of the invention is achieved by means of the material structure comprising a liquid-pervious cover layer, a liquid-impervious cover layer, and an absorbent structure enclosed between the cover layers, wherein the absorbent structure comprises polylactide fibres or filaments, the properties of which contribute to a rapid acquisition of liquid through the liquid-pervious cover layer for absorption into the absorbent structure also when the material structure is subjected to repeated wettings.

A second object of the present invention is to provide a material structure for use in absorbent articles having a liquid-acquiring layer, which enables a liquid-pervious cover layer to be bonded via the liquid-acquiring layer to an underlying liquid-distributing and/or liquid-storing layer by means of thermobonding at a relatively low temperature and without any separate adhesive, in order to provide an improved contact and liquid transport between the layers included in the material structure, and in which material structure the liquid-acquiring layer also provides a high degree of biological degradability in the short term.

In accordance with claim 2, this second object of the invention is achieved by means of the absorbent structure comprising a liquid-acquiring layer located closest to the liquid-pervious cover layer, and at least one liquid-distributing and/or liquid-storing layer located closest to the liquid-impervious cover layer, wherein the liquid-acquiring layer primarily is constituted of polylactide fibres or filaments.

A third object of the present invention is to provide an absorbent article, which when, used provides a high liquid-acquisition ability and which also provides a high degree of user comfort without any risk that the user gets a skin irritation, since the liquid-pervious cover layer remains dry also after repeated wettings.

In accordance with claim 9, this third object of the invention is achieved by means of the absorbent article comprising a liquid-pervious cover layer, a liquid-impervious cover layer, and an absorbent structure enclosed between the cover layers, wherein the absorbent structure comprises polylactide fibres or filaments, the properties of which contribute to a rapid acquisition of liquid through the liquid-pervious cover layer for absorption into the absorbent structure also when the article is subjected to repeated wettings.

Further objects of the invention will become evident from the following description, wherein the attached dependent claims define how these farther objects are achieved.

BRIEF DESCRIPTION OF THE DRAWINGS

In the following, the invention will be described with reference to the attached drawing, in which.

EXAMPLE 1

Contact Angle Measurement on Single Fibres

Figure 1:
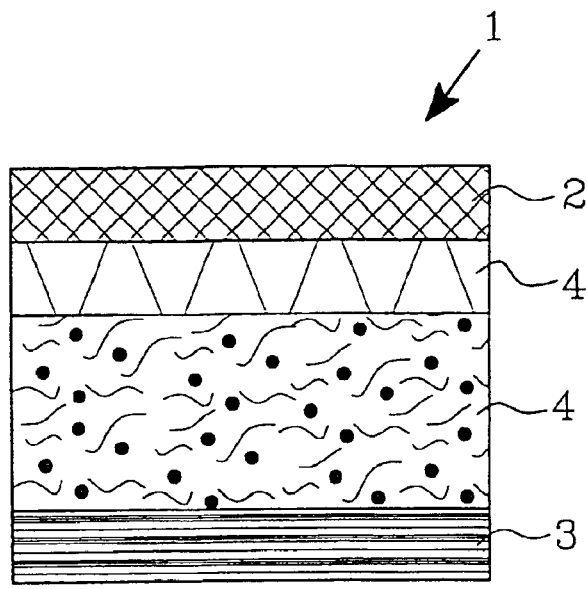
FIG. 1 shows a schematic cross-sectional view of a preferred embodiment of a material structure according to the invention.

In order to illustrate the invention, and using apparatus which is well known to the skilled person, a series of measurements of contact angles on single fibres from two different nonwoven materials, intended to be used as liquid-acquiring layers in a material structure for use in an absorbent article, was performed.

The measurements were performed using Wilhelmy's method, wherein the contact angles were determined by means of a balance scale manufactured by Cahn Instruments in California, U.S.A. The model of the balance scale which was used is DCA-322, wherein DCA means "Dynamic Contact Angle". A personal computer, Compac 386/20, was utilised for controlling the instrument The personal computer also was utilised for recording measurement data and for performing the subsequent calculations.

The measurements with the above-mentioned apparatus are performed by means of suspending a fibre vertically in the extremely sensitive balance scale, wherein a liquid container is placed on a movable table right below the fibre. By means of raising the table, the liquid surface is brought closer in order to eventually get into contact with the fibre. A liquid meniscus, which will act on the partially immersed fibre with a vertical force, is formed around the fibre when the fibre is dipped into the liquid.

The vertical force which acts on the fibre can either be positive or negative, depending on the surface properties of the fibre and the liquid. An attractive force, i.e. a positive force, is created when the contact angle between fibre and liquid is smaller than 90°. In case the fibre-liquid system exhibits a contact angle which is larger than 90°, which for example is the case when a polypropylene fibre is dipped into water, liquid and fibre will repel each other instead, wherein the force becomes negative. By means of recording the reading on the balance scale, the attractive or repelling force can be determined.

The attractive or repelling force determined by means of the balance scale is related to the contact angle in accordance with:

$$F = \gamma_L \, p \, \cos\theta + m \, g - \rho_L \, l \, g \, A;$$

wherein
F=measured force [N]
$\gamma_L$ =surface energy of the liquid [J/m2]
p=fibre circumference [m]
θ=contact angle in the boundary surface fibre-liquid-air [°]
m=weight of the mounted fibre [kg]
g=the gravitational constant [m/s$^2$]
$\rho_L$=liquid density [kg/m$^3$]
l=wetted fibre length [m]
A=cross-sectional area of the fibre [m$^2$]

The contact angle in the equation relates to an average calculated from the entire circumference of the fibre. The second term in the equation represents the weight of the mounted fibre, wherein the third term in the equation is the reduction of the fibre weight resulting from displaced liquid volume. Normally, both these terms are taken into account in a computer calculation program for contact angle determination, which results in the equation being simplified to:

$$F = \gamma_L p \cos\theta$$

The value of the advancing contact angle $\theta_a$ is determined when the fibre is dipped into the liquid, whereas the receding contact angle $\theta_r$ is determined when the fibre is pulled out from the liquid. Since the contact angles $\theta_a$, $\theta_r$ are dependent on the velocity of the liquid front, it is important that the above-mentioned movable table is raised and lowered with a constant speed, and that the speed is sufficiently low in order to enable the system to reach equilibrium in each point during the measurement Furthermore, the measurement is performed at a defined temperature and humidity in the sample chamber, and with protecting screens around the movable table which prevent air draughts, dust or the like from disturbing the measurements. Furthermore, the movable table is placed on a support which is protected from vibrations.

The balance scale utilised for the measurements has three scales, out of which two provide different measurement accuracies, and the third is utilised for taring with counter-weights.

In the measurements in question, the scale with the highest measurement accuracy, namely $10^{-6}$ g, was utilised. The table on which the liquid container is placed is raised and lowered by means of an electric motor, wherein the speed of the table can be controlled via the connected computer and be displayed on the computer display before a measurement starts. Before measurement commences, the surface energy of the utilised liquid and the fibre circumference have to be fed into the calculation program of the computer.

When performing a measurement, the fibre for which contact angles are to be determined is mounted onto a piece of adhesive tape leaving a portion of the fibre free, after which the adhesive tape with its attached fibre is clamped in a metal clamp which is suspended in the scale with the highest measurement accuracy. Before this, the balance scale has been tared with only the metal clamp suspended in the scale with the highest measurement accuracy. After this, the liquid container placed on the movable table below the fibre is filled with test liquid having a known surface energy. Before the measurement commences, the fibre has to be suspended perpendicularly to the liquid surface below, and be absolutely still so that the balance scale shows a stable value. When this condition has been achieved, the table with the liquid container is raised until the liquid surface is approximately 1 mm from the end of the fibre suspended in the scale.

During the measurement, the computer initially detects a base line, whereafter the table is raised with a constant, predetermined speed. Thereby, the fibre has to be sufficiently stiff in order to remain vertical also after having penetrated the liquid surface. When one or a few millimetres of the fibre has/have been dipped into the liquid, the computer is ordered to stop the table, whereafter the lowering of the table starts. During the measurement, variations in the force measured via the balance scale and calculated by the computer can be detected on the computer display. When the measurement is finished, representative portions of the advancing and the receding force curve are selected, whereafter the calculation program of the computer calculates the desired contact angles by means of the above-discussed Wilhelmy's equation.

By means of the above-described method, contact angles of polyester fibres which normally are used in liquid-acquiring layers were compared to contact angles of polyester fibres based on polylactide.

Two of the evaluated fibres (A, B) were polyester fibres from a conventional, commercially avaliable, through-air bonded liquid-acquiring layer. Such a liquid-acquiring layer consists of 35 weight-% polyester fibres with the denomination UNITIKA 4080 (A) and 65 weight-% polyester fibres with the denomination Trevira T200(B).

The third evaluated fibre (C) was a polylactide fibre (PLA) with 99 weight-% L-polylactide and 1 weight-% D-polylactide. Normally, such a high proportion of the L-form is utilised when manufacturing fibres.

Five measurements were performed on each fibre type (A–C), wherein the fibres first were dipped into water for determination of the contact angles $\theta_{a0}$ and $\theta_{r0}$. After finished measurement, the fibres were allowed to remain suspended in the measurement equipment during 5 minutes in wetted condition in contact with the ambient air, after which the fibres once again were dipped into water for determination of the contact angles $\theta_{a5}$ and $\theta_{r5}$. The obtained results are evident from the table below:

| Fibre | $\theta_{a0}$ | $\theta_{r5}$ | $\theta_{r0}$ | $\theta_{r5}$ |
|---|---|---|---|---|
| fibre A, Unitika 4080 | 68° | 77° | 50° | 53° |
| fibre B, Trevira 7200 | 71° | 79° | 55° | 54° |
| fibre C, PLA | 58° | 73° | 34° | 37° |

All three fibres were treated with a hydrophilic surfactant before the contact angle measurements were performed. The reason why $\theta_{a5}$ is higher than $\theta_{a0}$ for all three fibres is that the surfactant at least partially is washed away from the fibre surface during the wetting, so that $\theta_{a5}$ primarily is representative for the polymer surface itself. The fact that the receding contact angles $\theta_{r0}$ and $\theta_{r5}$ are approximately equal for a certain fibre shows that the measurements both at 0 minutes and 5 minutes take place on essentially identical fibre surfaces, As is evident from the above-reported results, in particular the receding contact angles $\theta_{r0}$ and $\theta_{r5}$ are considerably lower for the polylactide fibre (C) than for the two conventional polyester fibres (A and B). Accordingly, the polylactide fibre has a more hydrophilic nature than the conventional polyester fibre, both after a few and after repeated wettings. This provides material structures according to the invention with polylactide fibres or filaments with a high, permanent liquid acquisition ability also if no or only a low addition of surfactant is utilised.

In addition to the above-reported advantages of polylactide fibres in comparison to conventional synthetic fibres, the surprising effect disclosed in Example 1 above constitutes the foundation of the present invention.

DETAILED DESCRIPTION OF PREFERRED EMBODIMENTS

In the attached FIG. 1, a schematic cross-sectional view of a preferred embodiment of a material structure according to the invention is shown. The structure in intended for use in absorbent articles, such as diapers or training pants for infants of incontinent adults, incontinence guards, sanitary napkins, pantyliners, or the like. It should be noted that the layer thicknesses depicted in FIG. 1 are entirely schematic.

The material structure 1 comprises a liquid-pervious cover layer 2, a liquid-impervious cover layer 3, and an absorbent structure 4, 4' enclosed between said cover layers 2, 3.

In the described embodiment, the liquid-pervious cover layer 2 is a spunbond-material, but can be of type suitable for the application, for example a nonwoven material, a textile material, a scrim material, a perforated plastic film, an apertured nonwoven material, or another suitable pervious material. The liquid-pervious cover layer 2 is advantageously based on polymers having a low intrinsic absorption capacity for body fluids, since it is desirable that the cover layer 2 remains as dry as possible also after repeated wettings of the material structure.

In the described embodiment, the liquid-impervious cover layer 3 is a polyethylene film, but it can be of any type suitable for the purpose, for example a plastic film or another liquid-impervious film.

According to the invention and the preferred embodiment, the absorbent structure 4, 4' included in the material structure according to the invention comprises polylactide fibres or filaments. When wetting the material structure 1, the properties of the polylactide fibres (PLA) or filaments will contribute to a rapid acquisition of liquid through the liquid-pervious cover layer 2 for absorption into the absorbent structure 4, 4', also if the material structure is subjected to repeated wettings.

The reason for this is that the PLA-fibres or filaments, in contrast to for example cellulosic fibres or filaments and in a similar way as conventional synthetic fibres, maintain their stiffness and thereby also the desired structure which has been designed when manufacturing the absorbent structure 4, 4' and that the PLA-fibres exhibit wetting properties which surprisingly enough are considerably better than for the conventional synthetic fibres based on crude oil. Therefore, the excellent wetting properties of the PLA-fibres gives the absorbent structure 4, 4' a high, permanent liquid-acquisition ability already at no or a low surfactant addition.

According to the preferred embodiment of the material structure according to the invention, the absorbent structure comprises a liquid-acquiring layer 4', and one or several liquid-distributing and/or liquid-storing layers 4. The liquid-acquiring layer 4' is located closest to the liquid-pervious cover layer 2, whereas the liquid-distributing/liquid-storing layer 4 is located closest to the liquid-impervious cover layer 3.

In the preferred embodiment, the liquid-acquiring layer 4' is primarily constituted of polylactide fibres or filaments, wherein the liquid-distributing/liquid-storing layer 4 primarily contains cellulose fluff pulp with an addition of highly absorbent synthetic polymers, so-called superabsorbents. The task of the liquid-acquiring layer 4' is to be able to efficiently receive large quantities of liquid which are transported through the liquid-pervious cover layer 2, and to rapidly forward the liquid to the underlying liquid-distributing and/or liquid-storing layer 4. In the described embodiment, the liquid-acquiring layer 4' is a fluffy nonwoven material with an open pore structure, and is constituted primarily of polylactide fibres or filaments. According to a preferred embodiment, the liquid-acquiring layer 4' is bonded by means of mechanical needling, but also other binding techniques, such as through-air binding or binding by means of water jets, can advantageously be utilised.

The liquid-acquiring layer 4' can advantageously be bonded by means of thermobonding in order to compact the layer as little as possible, and particularly advantageously by means of through-blowing hot air in a through-air binding process. However, as has become evident in the foregoing, it is also conceivable with embodiments of the material structure according to the invention which utilise a liquid-acquiring layer 4' which has been bonded in another suitable process.

It is of course also conceivable with embodiments of the material structure according to the invention, in which also fibres or filaments of another polymer than polylactide are included in the liquid-acquiring layer 4'.

The liquid-acquiring layer 4' can either be a bonded nonwoven layer or an unbonded, porous fibre wadding. It is conceivable with embodiments of the invention both with cut PLA-staple fibres and/or continuous PLA-filaments (so-called tow).

In an alternative embodiment of the material structure according to the invention, also the liquid-distributing and/or liquid-storing layer 4 comprises polylactide fibres or filaments. In this embodiment, the polylactide fibres can function as reinforcement fibres, and thereby decrease the risk for wet collapse of the liquid-distributing/liquid-storing layer 4.

In another embodiment of the invention, the polylactide fibres or filaments function as binder fibres in the absorbent structure 4, 4'. In this embodiment, the polylactide fibres provide thermal bonds between the fibres within the liquid-acquiring layer 4' and/or within the liquid-distributing/liquid-storing layer 4. Furthermore, the polylactide fibres function as binder fibres when two different layers are bonded together by means of thermobonding.

This, for example, enables the liquid-acquiring layer 4' to be bonded to the liquid-distributing/liquid-storing layer 4 and/or that the liquid-acquiring layer 4' or the liquid-distributing/liquid-storing layer 4 is bonded to its outside cover layer 2, 3. When bonding the absorbent structure 4, 4' to outside cover layers, it is advantageous if also the cover layers 2, 3 comprise a certain proportion of polylactide fibres.

In embodiments where the polylactide fibres are utilised as binder fibres for binding a layer or for binding several layers together, the different layers can for example contain bicomponent fibres formed from two different lactides with different melting temperatures, fibres containing copolymers of polylactide, or mixtures of two different types of lactide fibres with different properties.

Figure 2:
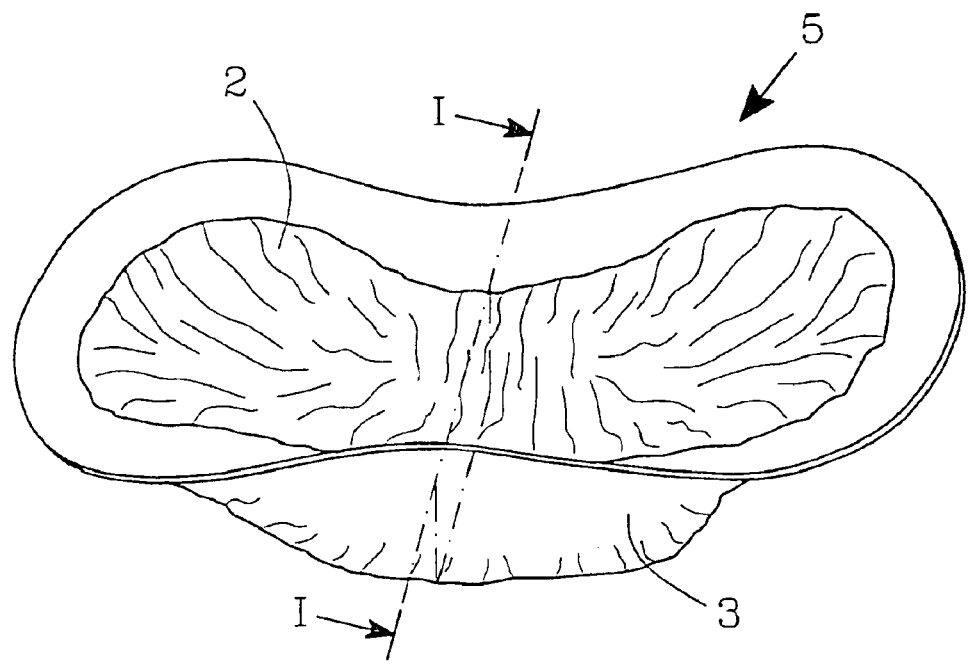
FIG. 2 shows a schematic perspective view of an absorbent article according to a preferred embodiment of the invention, in which article the material structure shown in FIG. 1 is included, and the cross-section depicted in FIG. 1 has been indicated with dotted lines.

In the following, a preferred embodiment of an absorbent article according to the invention will be described with reference to the attached FIG. 2, and when applicable to FIG. 1. Thereby, it should be noted that the article shown in FIG. 2 only is a schematic depiction, and that embodiments of the invention in which the article has another shape or appearance than what is shown in the figure of course are conceivable.

In the absorbent article 5, a material structure 1 comprising a liquid-pervious cover layer 2, a liquid-impervious cover layer 3, and an absorbent structure 4, 4' enclosed between said cover layers, are included.

According to the invention and the preferred embodiment, the absorbent structure 4, 4' comprises polylactide fibres or filaments, the properties of which contribute to a rapid acquisition of liquid through the liquid-pervious cover layer 2 for absorption into the absorbent structure 4, 4' also when the article is subjected to repeated wettings.

Thanks to the above-mentioned features, the absorbent article 5 provides a high liquid acquisition ability when used without any risk that the user gets skin irritation and, furthermore, a high decree of user comfort, since the liquid-pervious cover layer 2 remains dry also after repeated wettings. Furthermore, the use of polylactide fibres gives the absorbent article 5 a higher proportion of material which is biologically degradable in the short term, and is advantageous also because the polylactide fibres or filaments are based on renewable raw materials.

Accordingly, the absorbent article 5 according to the invention comprises a material structure 1 according to the invention in accordance with what has been described in the foregoing, and is particularly advantageously designed as a disposable baby diaper, a pair of training pants, an incontinence diaper, a pair of diaper pants for incontinent adults, an incontinence guard, a sanitary napkin, or a pantyliner.

The present invention should by no means be regarded as being limited to what has been described above in connection with the different embodiments, or to what is shown in the attached drawings, but the scope of the invention is defined by the following claims.

Furthermore, the polylactide fibres or filaments utilised in accordance with the invention are degradable in the short term and based on a raw material which is renewable in the short term and easily available, i.e. lactic acid. In order to facilitate thermobonding, the utilised polylactide polymer is advantageously of a type having a comparatively low melting temperature. Fibre thickness, fibre length, and fibre cross-section of the PLA-fibres or filaments have to be adapted to the application in question.

We claim:

1. A material structure for use in absorbent articles comprising
    a liquid-pervious cover layer,
    a liquid-impervious cover layer, and
    an absorbent structure enclosed between said cover layers,
    wherein the absorbent structure comprises polylactide fibres or filaments which contribute to a rapid acquisition of liquid through the liquid-pervious cover layer for absorption into the absorbent structure when the material structure is subjected to repeated wettings,
    wherein the absorbent structure comprises a liquid-acquiring layer located closest to the liquid-pervious cover layer, and at least one liquid-distributing and/or liquid-storing layer located closest to the liquid-impervious cover layer, and
    wherein the liquid-acquiring layer is constituted primarily of polylactide fibres or filaments.

2. A material structure according to claim 1, wherein the liquid-acquiring layer has comprises a nonwoven layer or a porous fibre wadding.

3. A material structure according to claim 1, wherein the liquid-acquiring layer has been bonded by means of thermobonding.

4. A material structure according to claim 1, wherein the liquid-acquiring layer has been thermobonded by means of through-blowing hot air in a through-air binding process.

5. A material structure of according to claim 1, wherein the liquid-acquiring layer has been bonded by means of needling with water jets in a hydroentangling process.

6. A material structure according to claim 1, wherein the liquid-distributing and/or liquid-storing layer comprises polylactide fibres or filaments.

7. A material structure according to claim 1, wherein a proportion of the polylactide fibres or filaments in the absorbent structure functions as binder fibres in the absorbent structure.

8. An absorbent article comprising a material structure, the material structure comprising a liquid-pervious cover layer, a liquid-impervious cover layer and an absorbent structure enclosed between said cover layers,
    wherein the absorbent structure comprises polylactide fibres or filaments which contribute to a rapid acquisition or liquid through the liquid-pervious cover layer for absorption into absorbent structure when the article is subjected to repeated wettings.

9. An absorbent article including a material structure comprising a liquid-pervious cover layer, a liquid-impervious cover layer and an absorbent structure inclosed between said cover layers,
    wherein the absorbent structure comprises polylactide fibres or filaments which contribute to a rapid acquisition or liquid through the liquid-pervious cover layer for absorption into the absorbent structure when the article is subjected to repeated wettings,
    the absorbent article comprising a material structure according to claim 1, and the absorbent article being a disposable baby diaper, a pair of training pants, an incontinence diaper, a pair of diaper pants for incontinent adults, an incontinence guard, a sanitary napkin, or a pantyliner.

10. A material structure according to claim 1, wherein fibers or filiaments of the liquid-acquiring layer are bonded to each other by means of mechanical needing.

11. A material structure for use in absorbent articles as in claim 1, wherein the absorbent article is a diaper, training pant, incontinence guard, sanitary napkin, or pantyliner.

* * * * *